United States Patent [19]

Schreiber et al.

[11] 3,974,137

[45] Aug. 10, 1976

[54] PROCESS FOR THE PREPARATION OF 1-[L-(−)-γ-AMINO-α-HYDROXYBUTYRYL]-KANAMYCIN A (RD-1341A)

[75] Inventors: Richard Henry Schreiber, Canastota; John Gerard Keil, Manlius, both of N.Y.

[73] Assignee: Bristol-Myers Company, New York, N.Y.

[22] Filed: May 23, 1974

[21] Appl. No.: 472,781

Related U.S. Application Data

[63] Continuation-in-part of Ser. No. 330,377, Feb. 7, 1973, abandoned.

[52] U.S. Cl. .......................... 536/10; 260/210 AB; 536/17
[51] Int. Cl.[2] ................. A61K 31/71; C07H 15/22
[58] Field of Search .................. 260/210 AB, 210 K

[56] References Cited

UNITED STATES PATENTS

| | | | |
|---|---|---|---|
| 3,781,268 | 12/1973 | Kawaguchi et al. | 260/210 AB |
| 3,792,037 | 2/1974 | Kawaguchi et al. | 260/210 AB |
| 3,796,699 | 3/1974 | Naito et al. | 260/210 AB |
| 3,832,286 | 8/1974 | Weinstein et al. | 260/210 AB |
| 3,852,264 | 12/1974 | Weinstein et al. | 260/210 AB |
| 3,868,360 | 2/1975 | Daniels et al. | 260/210 AB |

*Primary Examiner*—Johnnie R. Brown
*Attorney, Agent, or Firm*—Robert E. Havranek

[57] ABSTRACT

1-[L-(−)-γ-amino-α-hydroxybutyryl]-kanamycin A is a compound useful as an antibacterial agent. A new process for its preparation has been developed which comprises using aldehyde blocking agents on the amine functions prior to acylation with L-(−)-γ-amino-α-hydroxybutyric acid.

5 Claims, No Drawings

PROCESS FOR THE PREPARATION OF 1-[L-(−)-γ-AMINO-α-HYDROXYBUTYRYL]-KANAMYCIN A (RD-1341A)

CROSS-REFERENCE TO RELATED APPLICATION

This application is a continuation-in-part of a copending application Ser. No. 330,377, filed Feb. 7, 1973, now abandoned.

BACKGROUND OF THE INVENTION

1. Field of the Invention

This invention relates to a new process for the preparation of a semisynthetic 1-substituted derivative of kanamycin A, said compound being prepared by acylating the 1-amino-function of kanamycin A with a γ-amino-α-hydroxybutyryl moiety after selectively blocking the amine functions.

2. Description of the Prior Art

Kanamycin A is a known antibiotic described in Merck Index, 8th Edition, pp. 597–598. Kanamycin A is a compound having the formula

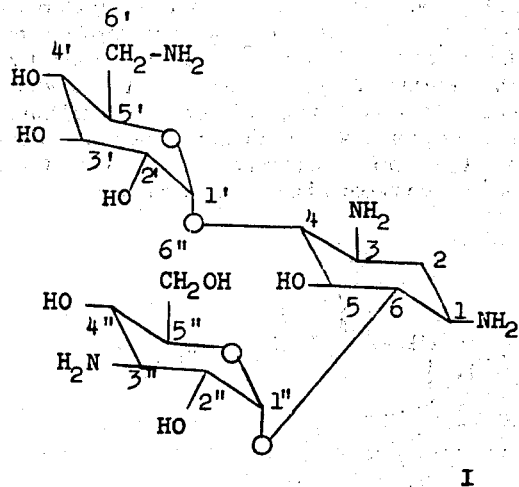

I

SUMMARY OF THE INVENTION

The compound having the formula

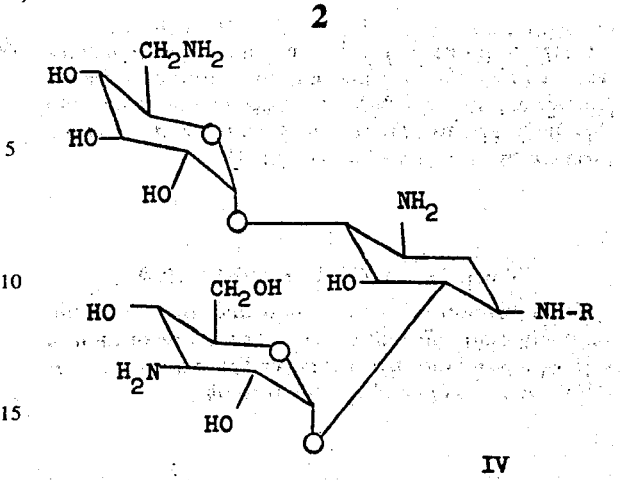

IV in which R is L-(−)-γ-amino-α-hydroxybutyryl is prepared by the process which comprises the consecutive steps of A. acylating one mole of kanamycin A with one mole or less of N-(benzyloxycarbonyloxy)succinimide to produce the compound having the formula

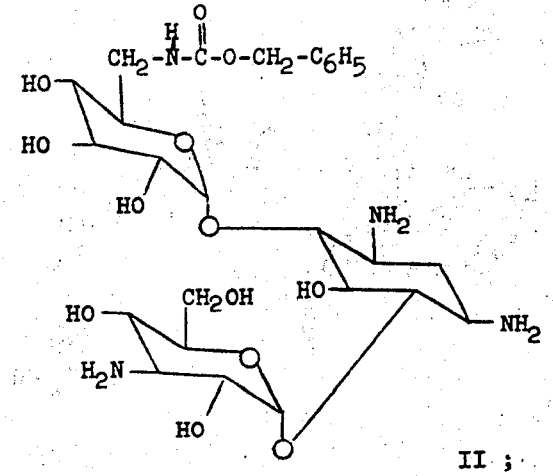

II ;

B. treating one mole of compound II with at least three moles of p-nitrobenzaldehyde to produce the compound having the formula

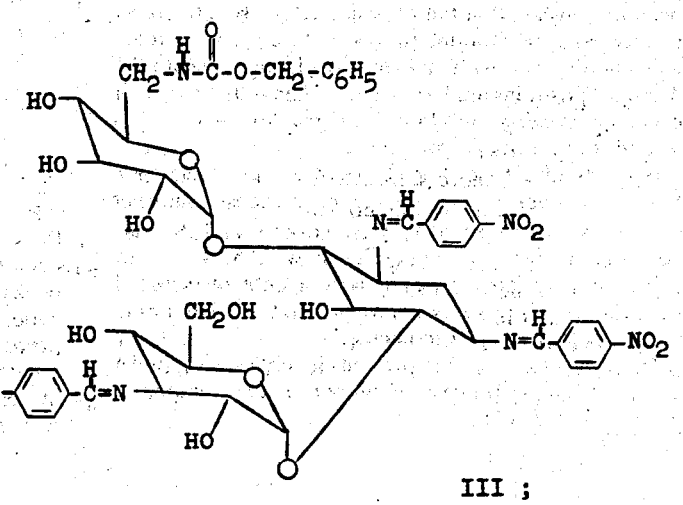

III ;

C. treating one mole of compound III with at least one mole of L-(-)-γ-benzyloxycarbonylamino-α-hydroxybutyric acid N-hydroxysuccinimide ester, and then hydrogenating the resultant intermediate in situ to produce the compound of formula IV.

DISCLOSURE OF THE INVENTION

This invention relates to a new and novel and substantially more efficient process for the preparation of 1-[L-(-)-γ-amino-α-hydroxybutyryl]-kanamycin A (IV), which compound has the formula

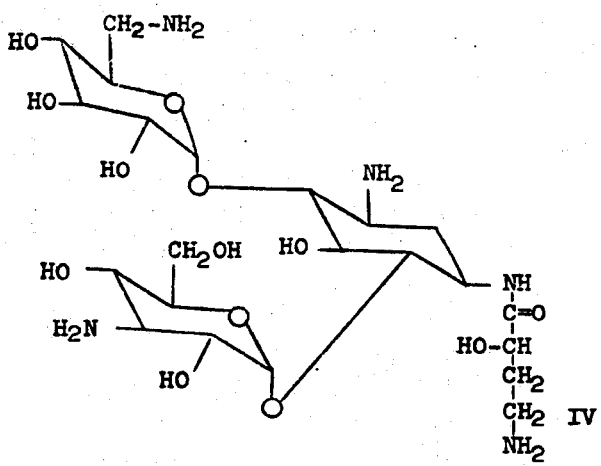

which process comprises the consecutive steps of

A. acylating one mole of kanamycin A with one mole or less of N-(benzyloxycarbonyloxy)succinimide, but preferably about one mole, in a solvent, preferably selected from the group comprising dimethylformamide, dimethylacetamide, tetrahydrofuran, dioxane, 1,2-dimethoxyethane, methanol, ethanol, water, acetone, pyridine, N-(lower)alkylpiperidine, or mixtures thereof, but preferably dimethylformamide, at a temperature below 50° C., and preferably below 25° C. to produce the compound having the formula

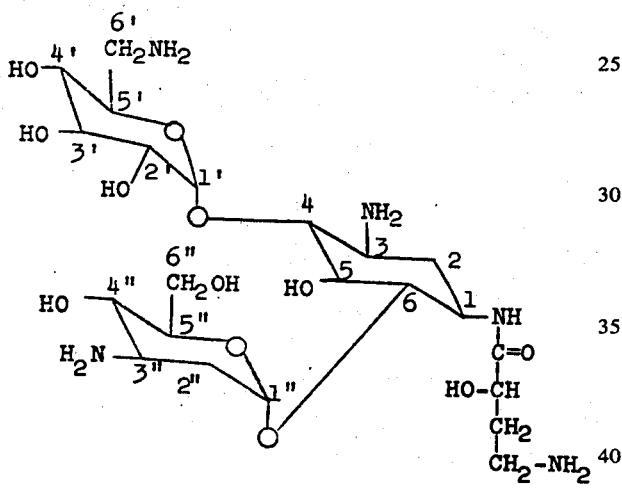

Kanamycin A possesses four primary amine functions at the 1, 3, 6' and 3" positions of the molecule. It has been established that the 6'-amine function is the most reactive and the 1-amine function is second most reactive when treated with an electrophylic agent. Both the 3 and 3" positions are less reactive than either the 1- or 6'-amine functions but do react to give low percentages of undesired acylated materials.

Accordingly, it was the object of the present invention to discover a more satisfactory process than that previously employed by our co-workers in U.S. Pat. Application Ser. No. 221,378, now U.S. Pat. No. 3,781,268, said process being more selectively directed to acylation of the 1-amine function to the other amine functions found in the molecule.

The objective of the present invention has been achieved by the process of preparing the compound having the formula

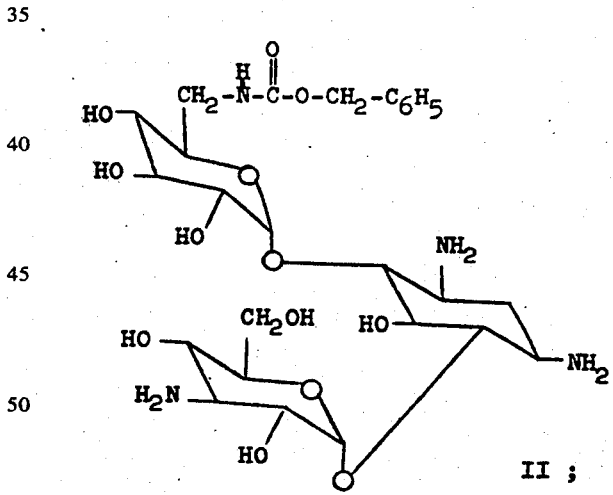

B. treating one mole of compound II with at least three moles of an aldehyde selected from the group comprising 4-nitrobenzaldehyde, salicylaldehyde, benzaldehyde, 4-methoxybenzaldehyde and pivalaldehyde, in absolute ethanol, methanol, n-propanol, isopropanol, n-butanol, sec-butanol, tert-butanol, or mixtures thereof, at about reflux temperatures, for a period of about two to five hours, to produce the compound having the formula

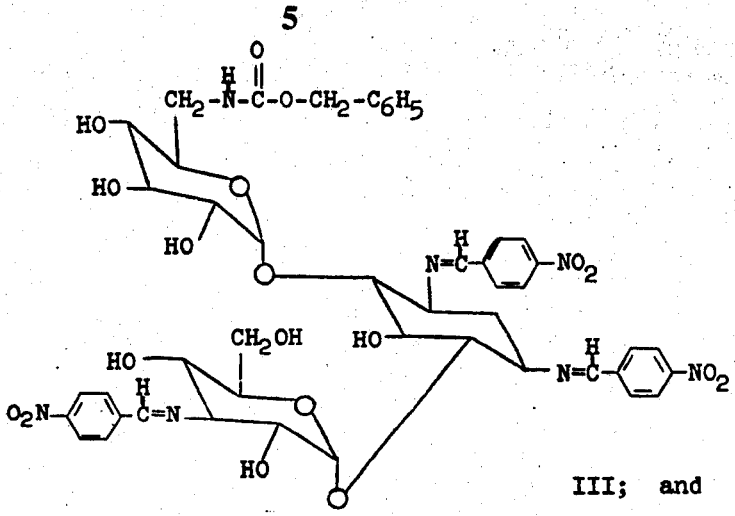

III; and

C. treating one mole of compound III with at least one mole of L-(−)-γ-benzyloxycarbonylamino-α-hydroxybutyric acid N-hydroxysuccinimide ester, but preferably in a ratio of about one to two moles of ester per mole of compound III, and most preferably at a ratio of about 1.0 to 1.3:1, in a solvent selected from the group comprising dimethylformamide, tetrahydrofuran, dimethylacetamide, propyleneglycol dimethyl ether, ethylene glycol dimethyl ether or dioxane, but preferably dimethylformamide, at a temperature in the range of 0° C. to about 50° C. but preferably at about room temperature, for a period of time till the acylation is complete, but for at least 5 hours; then removing the solvent and hydrogenating the residue in situ with hydrogen in the presence of a metal catalyst preferably selected from the group comprising palladium, platinum, Raney nickel, rhodium, ruthenium and nickel, but preferably palladium, and more preferably palladium on charcoal, in a water-water miscible solvent system, preferably selected from the group comprising water and dioxane, tetrahydrofuran, ethyleneglycol dimethyl ether, propyleneglycol dimethyl ether, or the like, but preferably 1:1 water-dioxane, and preferably in the presence of a catalytic amount of glacial acetic acid to produce the compound of formula IV.

Compound IV, 1-[L-(−)-γ-amino-α-hydroxybutyryl]-kanamycin A, possesses excellent antibacterial activity that appears superior to kanamycin A itself. Illustrated below are two tables showing the minimal inhibitory concentrations (MIC's) of kanamycin A and compound IVa (BB-K8) against a variety of gram-positive and gram-negative bacteria as obtained by the Steers agar-dilution method (Table I) and the two-fold dilution method (Table 2). Mueller-Hinton Agar Medium was used in the study of Table 1 and Heart Infusion Broth was used in the study of Table 2.

TABLE I (MIC mg./ml.)

| Organism | Kanamycin A (6-8198) | Compound IV [BB-K8] lot No. 4 |
|---|---|---|
| 1. Alk. faecalis A-9423 | 16 | 8 |
| 2. Alk. faecalis A-20648 | >125 | >125 |
| 3. Ent. cloacae A-0656 | .4 | 4 |
| 4. Ent. species A-20364 | >125 | 2 |
| 5. Ent. hafniae 1 A-20674 | 1 | 1 |
| 6. E. coli A-0636 | 2 | 1 |
| 7. E. coli A-20664 | 16 | 4 |
| 8. E. coli A-20665 | >125 | 1 |
| 9. E. coli A-20507 | 32 | 2 |
| 10. E. coli A-20520 | >125 | 4 |
| 11. E. coli A-20365 | >125 | 1 |
| 12. E. coli A-20684 | 2 | 2 |
| 13. E. coli A-20682 | >125 | 2 |
| 14. E. coli A-20683 | >125 | 8 |
| 15. E. coli A-20681 | 125 | 2 |
| 16. E. coli A-15119 | 4 | 4 |
| 17. K. pneumoniae A-0967 | 4 | 4 |
| 18. K. species A-20328 | >125 | 2 |
| 19. K. species A-20330 | 32 | 32 |
| 20. K. species A-20634 | >125 | 4 |
| 21. K. pneumoniae A-20680 | >125 | 4 |
| 22. K. pneumoniae A-0077 | 1 | 1 |
| 23. Pr. mirabilis A-9900 | 2 | 2 |
| 24. Pr. morganii A-15153 | 2 | 2 |
| 25. Pr. vulgaris A-9555 | 2 | 1 |
| 26. Pr. rettgeri A-9636 | 0.25 | 0.25 |
| 27. Pr. mirabilis A-20645 | 4 | 4 |
| 28. Pr. mirabilis A-20454 | 2 | 2 |
| 29. Providencia stuartii A-20615 | 2 | 1 |
| 30. Providencia alkalifaciens A-20676 | 1 | 1 |
| 31. Ps. aeruginosa A-20229 | 32 | 2 |
| 32. Ps. aeruginosa A-0943A | 125 | 16 |
| 33. Ps. aeruginosa A-20653 | >125 | 32 |

TABLE I-continued (MIC mg./ml.)

| Organism | Kanamycin A (6-8198) | Compound IV [BB-K8] lot No. 4 |
|---|---|---|
| 34. Ps. species A-20601 | 125, 63 | 16 |
| 35. Ps. species A-20621 | >125 | >125 |
| 36. Ps. maltophilia A-20620 | 32 | >125 |
| 37. Sal. enteritidis A-0531 | 1 | 0.5 |
| 38. Sal. derby A-20087 | >125 | 1 |
| 39. Ser. marcescens A-20019 | 2 | 4 |
| 40. Ser. marcescens A-9933 | 4 | 8 |
| 41. Ser. marcescens A-20460 | >125 | 4, 2 |
| 42. Ser. marcescens A-20459 | 4 | 16 |
| 43. Shig. flexneri A-9684 | 4 | 4 |
| 44. Aeromonas sp. A-20670 | 2 | 2 |
| 45. Arizona sp. A-20671 | 2 | 1 |
| 46. Citrobacter sp. A-20673 | 4 | 4 |
| 47. Edwardsiella sp. A-20678 | 4 | 4 |
| 48. Staph. aureus A-9606 | 1 | 1 |
| 49. Staph. aureus A-4749 | 0.5 | 1 |
| 50. Staph aureus A-9537 | .2 | 1 |
| 51. Staph aureus A-20610 | >125 | 2 |
| 52. Staph aureus A-20240 | >125 | 8 |
| 53. Staph aureus A-15197 | 1 | 2 |
| Mueller-Hinton Medium +4% sheep blood | | |
| 54. Str. faecalis A-9854 | 63 | 63 |
| 55. Str. faecalis A-9575 | 125 | >125 |
| 56. Str. pyogenes A-20200 | 32, 16 | 32 |
| 57. Str. pyogenes A-9604 | 125 | 125 |
| 58. Str. pyogenes A-15040 | 125 | 125 |
| 59. Str. pyogenes A-20065 | 125 | 125 |
| 60. D. pneumoniae A-9585 | 63, 32 | 63 |
| 61. D. pyogenes A-20159 | 125 | >125 |

TABLE 2

(MIC mg./ml.)

| Organism | Kanamycin A (6-8196) | Compound IV [BB-K8] lot No. 4 |
|---|---|---|
| 1. D. pneumoniae ±5% serum A-0585 | 63 | 63 |
| 2. Str. pyogenes±5% serum A-9604 | 125 | 125 |
| 3. Staph. aureus Smith A-9537 | 0.5 | 0.5 |
| 4. Staph. aureus A-9497 | 0.5 | 0.5 |
| 5. Staph. aureus A-20239 | 125 | 4 |
| 6. Staph. aureus A-20240 | 125 | 4 |
| 7. Enter. cloacae A-0656 | 2 | 2 |
| 8. Enter. species A-20364 | 125 | 2 |
| 9. K. pneumoniae A-9867 | 2 | 4 |
| 10. E. coli K-12 ML1410 A-20361 | 2 | 4 |
| 11. E. coli K-12 ML1630 A-20363 | 125 | 2 |
| 12. E. coli K-12 A-9632 | 2 | 1 |
| 13. E. coli A-20664 | 32 | 8 |
| 14. E. coli A-20665 | 125 | 8 |
| 15. Pr. mirabilis A-9900 | 2 | 16 |
| 16. Pr. morganii A-15153 | 4 | 16 |
| 17. Pr. vulgaris A-9436 | 1 | 2 |
| 18. Ps. aeruginosa A-20227 | 4 | 1 |
| 19. Ps. species A-20499 | 63 | 4 |
| 20. Ps. aeruginosa A-20653 | 125 | 4 |
| 21. Ps. species A-20621 | 125 | 125 |
| 22. Ser. marcescens A-20019 | 2 | 4 |
| 23. Ser. marcescens A-20141 | 16 | 16 |

The above MIC data show that compound IV (BB-K8) is superior to kanamycin A in activity, particularly against kanamycin A resistant organisms.

The MIC data also correlate well with the in vivo results for all three organisms against which kanamycin A and compound IV were tested.

Compound IV and kanamycin A were equally effective in infections of mice caused by kanamycin A-sensitive strains of E. coli A-15119 and Staph. aureus A-9537. Although the CD$_{50}$ values (currative dose in 50% of mice lethally infected) for Staph. aureus A-9537 suggest that compound IV is slightly less active than kanamycin A; this small difference is probably not significant because the dose levels were far apart (5X dilution).

Against the kanamycin-resistant strain of E. coli A-20520, kanamycin A as expected, was not very effective in vivo, whereas compound IV demonstrated a marked protective action. Compound IVa was approximately 10 times more active against this E. coli strain when administered in a 4-treatment regimen rather than in a 2-treatment one.

TABLE 3

A comparison of In Vitro and In Vivo Activities of Compound IV and Kanamycin A

| Compounds | Test Number | Staphylococcus aureus A-9537 | | Escherichia coli A-15119 | | Escherichia coli A-20520 | |
|---|---|---|---|---|---|---|---|
| | | MIC | $CD_{50}$[b] | MIC | $CD_{50}$ | MIC | $CD_{50}$ |
| Compound IV | 1 | 1 | 2.0 × 2 | 2 | 2 × 2 | 2 | 66 × 2 |
| | 2 | —[c] | — | — | — | — | 5 × 4 |
| Kanamycin A | 1 | 2 | 0.5 × 2 | 4 | 4 × 2 | 125 | 200 × 2 |
| | 2 | — | — | — | — | — | 200 × 4 |

[a]MIC =minimum inhibitory concentration (μg./ml.). Tests conducted as described by Chisholm et al., (Antimicrob. Agents and Chemotherapy-1969, p. 244, 1970) using Mueller-Hinten agar as the test medium.
[b]$CD_{50}$ =curative dose, 50% (mg./kg./treated × number of treatments). Mice were treated subcutaneously at 1 and 4 hours post-infection when 2 treatment were administeredand at 0, 2, 4 and 6 hours post-infection when 4 treatment weree given.Other aspects of the test were carried out as described by Price et al. (J. ofAntibiotics 22:1. 1969).
[c]— = not tested.

Compound IV is valuable as an antibacterial agent, nutritional supplement in animal feeds, therapeutic agent in poultry and animals, including man, and is especially valuable in the treatment of infectious diseases caused by Gram-positive and Gram-negative bacteria.

Compound IV, when administered orally, is useful as an adjunctive treatment for preoperative sterilization of the bowel. Both aerobic and anaerobic flora which are suseptible to this drug are reduced in the large intestine. When accompanied by adequate mechanical cleansing, it is useful in preparing for colonic surgery.

Compound IV is effective in the treatment of systemic bacterial infections in man when administered parenterally in the dosage range of about 250 mg. to about 3000 mg. per day in divided doses three or four times a day. Generally the compound is effective when administered at a dosage of about 5.0 to 7.5 mg./kg. of body weight every 12 hours.

A preferred embodiment of the present invention is the process for the preparation of the compound having the formula

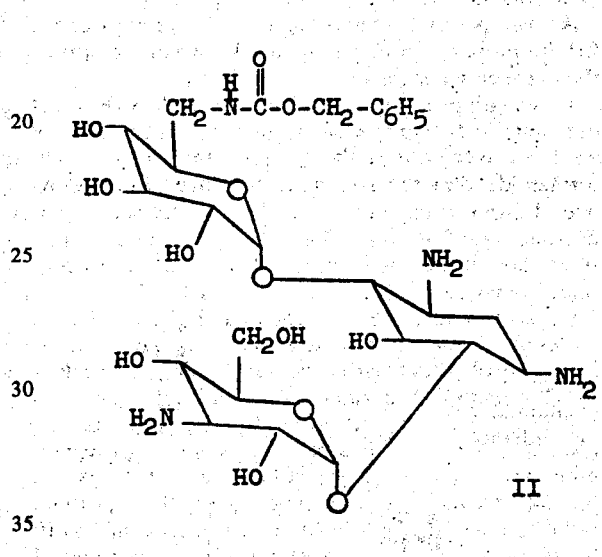

which comprises the consecutive steps of

A. acylating one mole of kanamycin A with one mole or less of N-(benzyloxycarbonyloxy)succinimide, in a solvent, at a temperature of below 50° C., to produce the compound having the formula B. treating one mole of compound II with at least three moles of an aldehyde selected from the group comprising 4-nitrobenzaldehyde, salicylaldehyde, benzaldehyde, 4-methoxybenzaldehyde and pivaldehyde, in a (lower)alkanol, at elevated temperatures, for at least two hours, to produce the compound having the formula

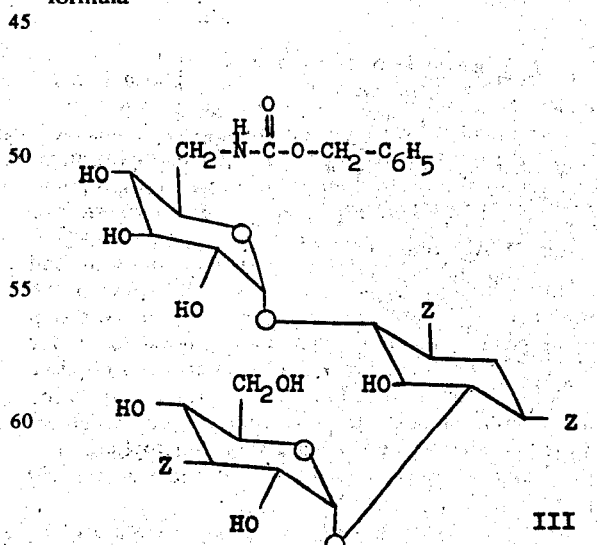

in which Z is a radical of the formula

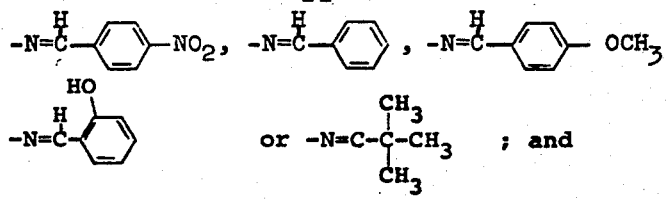

C. treating one mole of compound III with at least one mole of L-(−)-γ-benzyloxycarbonylamino-α-hydroxybutyric acid N-hydroxysuccinimide ester, in an organic solvent at a temperature in the range of 0° C. to about 50° C.; then removing the solvent and hydrogenating the residue with hydrogen in a water-water miscible solvent system to produce com-IV.

A more preferred embodiment is the process above for the preparation of compound IV which comprises the consecutive steps of A. acylating one mole of kanamycin A with about one mole of N-(benzyloxycarbonyloxy)succinimide, in a solvent selected from the group comprising dimethylformamide, dimethylacetamide, tetrahydrofuran, dioxane, 1,2-dimethoxyethane, methanol, ethanol, water, acetone, pyridine, an N-(lower)alkylpiperidine, or mixtures thereof, at a temperature below 25° C., to produce compound II;

B. treating one mole of compound II with 3 to 6 moles of an aldehyde selected from the group comprising 4-nitrobenzaldehyde, benzaldehyde, salicylaldehyde, 4-methoxybenzaldehyde and pivaldehyde, in a (lower)alkanol selected from the group comprising absolute ethanol, methanol, n-propanol, isopropanol, n-butanol, sec-butanol tert-butanol, or mixtures thereof, at temperatures in the range of 50° C. to about reflux temperature of the system, for a period of 2 to 10 hours, to produce compound III in which Z is a radical of the formula

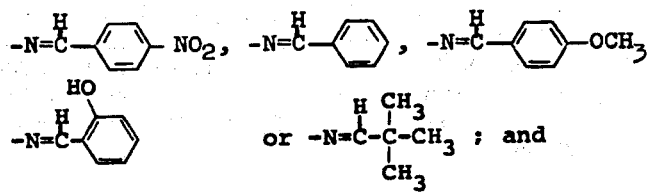

C. treating one mole of compound III with 1 to 1.3 moles of L-(−)-γ-benzyloxycarbonylamino-α-hydroxybutyric acid N-hydroxysuccinimide ester, in a solvent selected from the group comprising dimethylformamide, tetrahydrofuran, dimethylacetamide, propyleneglycol dimethyl ether, ethyleneglycol dimethyl ether or dioxane, at a temperature in the range of about 10° C. to about 35° C.; removing the solvent in vacuo and hydrogenating the residue in situ with hydrogen in the presence of a metal catalyst selected from the group comprising palladium, platinum, rhodium, raney nickel, ruthenium and nickel, in a water-water miscible solvent system selected from the group comprising water and dioxane, tetrahydrofuran, ethyleneglycol dimethyl ether and propyleneglycol dimethyl ether, in the presence of a catalytic amount of glacial acetic acid to produce compound IV.

A most preferred embodiment is the process for the preparation of compound IV which comprises the consecutive steps of A. acylating one mole of kanamycin A with about one mole of N-(benzyloxycarbonyloxy)succinimide in dimethylformamide at a temperature in the range of about −20° C. to about 10° C. to produce compound II;

B. treating one mole of compound II with 3.5 to 4.5 moles of p-nitrobenzaldehyde or salicylaldehyde or benzaldehyde in absolute ethanol, methanol, n-propanol or isopropanol at about reflux temperature for a period of about 2 to 4 hours to produce compound III in which Z is a radical of the formula

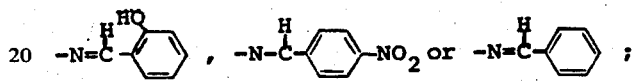

and

C. treating one mole of compound III with about 1.1 to about 1.3 moles of L-(−)-γ-benzyloxycarbonylamino-α-hydroxybutyric acid N-hydroxysuccinimide ester in dimethylformamide at about room temperature for at least 5 hours; then removing the solvent in vacuo and hydrogenating the residue in situ with hydrogen in the presence of palladium on charcoal in a 1:1 mixture of dioxane and water in the presence of a catalytic amount of glacial acetic acid to produce compound IV.

A most preferred embodiment is the process for the preparation of compound IV which comprises the consecutive steps of A. acylating one mole of kanamycin A with about one mole of N-(benzyloxycarbonyloxy)succinimide, in dimethylformamide at a temperature in the range of about −20° C. to about 10° C. to produce compound II;

B. treating one mole of compound II with about four moles of p-nitrobenzaldehyde in absolute ethanol at about reflux temperature for a period of about 2 to 4 hours to produce compound III in which Z is

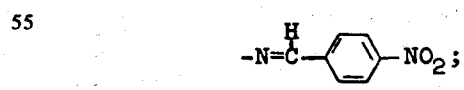

and

C. treating one mole of compound III with about 1.2 moles of L-(−)-γ-benzyloxycarbonylamino-α-hydroxybutyric acid N-hydroxysuccinimide ester in dimethylformamide, at about room temperature for at least 5 hours; then removing the solvent in vacuo and hydrogenating the residue in situ with hydrogen in the presence of palladium on charcoal in a 1:1 mixture of dioxane and water in the presence of a catalytic amount of glacial acetic acid to produce compound IV.

The most preferred embodiment is the process for the preparation of compound IV which comprises the consecutive steps of A. acylating one mole of kanamycin A with about one mole of N-(benzyloxycarbonyloxy)succinimide, in dimethylformamide at a temperature in the range of about −20° C. to about 10° C. to produce compound II;

B. treating one mole of compound II with about four moles of salicylaldehyde in absolute ethanol at about reflux temperature for a period of about 2 to 4 hours to produce compound III in which Z is

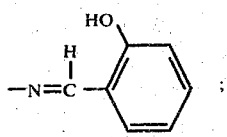

and

C. treating one mole of compound III with about 1.2 moles of L-(−)-γ-benzyloxycarbonylamino-α-hydroxybutyric acid N-hydroxysuccinimide ester in dimethylformamide, at about room temperature for at least 5 hours; then removing the solvent in vacuo and hydrogenating the residue in situ with hydrogen in the presence of palladium on charcoal in a 1:1 mixture of dioxane and water in the presence of a catalytic amount of glacial acetic acid to produce compound IV.

For the purpose of this disclosure, the term (lower)alkyl is an alkyl residue, straight or branched chain, of 1 to 6 carbons. (Lower)alkanol is a saturated alcohol, straight or branched chain, of 1 to 6 carbons containing one OH function.

EXAMPLES

EXAMPLE 1

Preparation of
L-(−)-γ-Benzyloxycarbonylamino-α-hydroxybutyric acid (VI)

L-(−)-γ-amino-α-hydroxybutyric acid (7.4 g., 0.062 mole) was added to a solution of 5.2 g. (0.13 mole) of sodium hydroxide in 50 ml. of water. To the stirred solution was added dropwise at 0°–5° C. over a period of 0.5 hour, 11.7 g. (0.068 mole) of carbobenzoxy chloride and stirring continued for one additional hour at the same temperature. The reaction mixture was washed with 50 ml. of ether, adjusted to pH 2 with dilute hydrochloric acid and extracted with four 80-ml. portions of ether. The ethereal extracts were combined, washed with a small amount of saturated sodium chloride solution, dried with anhydrous sodium sulfate and filtered. The filtrate was evaporated in vacuo and the resulting residue was crystallized from benzene to give 11.6 g. (74%) of colorless plates; melting point 78.5°–79.5° C., $[\alpha]_D = 4.5°$ (c=2, $CH_3OH$). Infrared (IR) [KBr]: IR (KBr)γc = 0 1740, 1690 cm$^{-1}$. Nuclear Magnetic Resonance (NMR) (acetone-$d_6$) δ (in ppm from TMS) 2.0 (2H,m), 3.29 (2H,d-d, J=6.7 and 12 Hz), 4.16 (1H,d-d, J=4.5 and 8 Hz), 4.99 (2H,s), 6.2 (2H, broad), 7.21 (5H,s).

Anal. calc'd. for $C_{12}H_{15}NO_5$: C, 56.91; H, 5.97; N, 5.53. Found: C, 56.66; H, 5.97; N, 5.47.

EXAMPLE 2

H-Hydroxysuccinimide ester of
L-(−)-γ-benzyloxycarbonylamino-α-hydroxybutyric acid (VII)

A solution of 10.6 g. (0.042 mole) of VI and 4.8 g. (0.042 mole) of N-hydroxysuccinimide[1] in 200 ml. of ethyl acetate was cooled to 0° C. and then 8.6 g. (0.042 mole) of dicyclohexylcarbodiimide was added. The mixture was kept overnight in a refrigerator. The dicyclohexylurea which separated was filtered off and the filtrate was concentrated to about 50 ml. under reduced pressure to give colorless crystals of VII which were collected by filtration; 6.4 g. m.p. 121°–122.5° C. The filtrate was evaporated to dryness in vacuo and the crystalline residue was washed with 20 ml. of a benzene-n-hexane mixture to give an additional amount of VII. The total yield was 13.4 g. (92%) $[\alpha]_D$ 1.5° (c=2, $CHCl_3$) IR (KBr) γc = 0 1810, 1755, 1740, 1680 cm$^{-1}$. NMR (acetone-$d_6$) δ (in ppm from TMS) 2.0 (2H, m), 2.83 (4H, s), 3.37 (2H, d-d, J=6.5 and 12.5 Hz), 4.56 (1H, m), 4.99 (2H, s), 6.3 (2H, broad), 7.23 (5H, s).

Anal. calc'd. for $C_{16}H_{18}N_2O_7$: C, 54.85; H, 5.18; N, 8.00. Found: C, 54.79, 54.70; H, 5.21, 5.20; M, 8.14, 8.12.

[1]. G. W. Anderson et al., J. Am. Chem. Soc., 86, 1839 (1964).

EXAMPLE 3

Preparation of N-(Benzyloxycarbonyloxy)succinimide

N-Hydroxysuccinimide[1] (23 g., 0.2 mole) was dissolved in a solution of 9 g. (0.22 mole) of sodium hydroxide in 200 ml. of water. To the stirred solution was added dropwise 34 g. (0.2 mole) of carbobenzoxy chloride with water-cooling and then the mixture was stirred at room temperature overnight to separate the carbobenzoxy derivative which was collected by filtration, washed with water and air-dried. Yield 41.4 g. (82%). Recrystallization from benzene-n-hexane (10:1) gave colorless prisms melting at 78–79° C.

[1]. G. W. Anderson et al., J. Am. Chem. Soc., 86, 1839 (1964).

EXAMPLE 4

Preparation of 6''-Carbobenzoxykanamycin A

A solution of 42.5 g. (90 m. moles) of kanamycin A free base in 450 ml. of water and 500 ml. of dimethylformamide (DMF) was cooled below 0° C. and stirred vigorously. To the solution was added dropwise over a period of about two hours a solution of 22.4 g. (90 m. mole) of N-(benzyloxycarbonyloxy)succinimide in 500 ml. of DMF. The mixture was stirred at −10° to 0° C. overnight and then at room temperature for one day. The reaction mixture was evaporated under reduced pressure below about 50° C. The oily residue was dissolved in a mixture of 500 ml. water and 500 ml. butanol, the mixture being filtered to remove insoluble material and separated into two layers. The butanol and aqueous layers were treated with butanol-saturated water (500 ml. × 2) and water-saturated butanol (500 ml. × 2), respectively, using a technique similar to counter current distribution. The three aqueous layers were combined and evaporated to dryness under reduced pressure to give an oily residue, a part of which crystallized on standing at room temperature. To the residue including the crystals was added about 100 ml.

of methanol, which dissolved the oil and separated it from the crystals. After adding about 300 ml. of ethanol, the mixture was kept at room temperature overnight to give a crystalline mass which was collected by filtration. It weighed 44 g. The product contained a small amount of kanamycin A as indicated by thin layer chromatography using n-propanol-pyridineacetic acid-water (15:10:3:12) as the solvent system and ninhydrin as the spray reagent.

The crude product was dissolved in 300 ml. of water and chromatographed on a column (30 mm. diameter) of CG-50 ion-exchange resin ($NH_4^+$ type, 500 ml.). The column was irrigated with 0.1 N ammonium hydroxide solution and the eluate was collected in 10-ml. fraction. The desired product was contained in tube numbers 10–100, while kanamycin A recovered from slower-moving fractions and the position isomer(s) of the product seemed to be contained in the faster-moving fractions. The fractions 10–110 were combined and evaporated to dryness under reduced pressure to give 24.6 g. (45%) of a colorless product 6-carbobenzoxykanamycin A (II) [6'-Cbz-kanamycin A], which began to melt and color at 204° C. and decomposed at 212° C. with gas evolution $[\alpha]_D$ +106° (c = 2 $H_2O$).

room temperature for 5 hours during which time fine needles crystallized out. The crystals were collected by filtration, washed with 50 ml. of ethanol and air-dried to obtain 30.1 g. (56%) of a diastereomer of the dehydroabietylamine salt. M.p. 93°–94° C. $[\alpha]_D^{24}$ +15° (c. 2.5, MeOH). Recrystallization from 300 ml. of ethanol gave 23.2 g. (43%) of the pure product. M.p. 94°–95° C. $[\alpha]_D^{24}$ +10.8° (c. 2.5, MeOH). Further recrystallization did not change the melting point and the specific rotation.

Anal. calc'd. for $C_{32}H_{42}N_2O_5 \cdot H_2O$: C, 69.54; H, 8.02; N, 5.07. Found: C, 69.58; H, 8.08; N, 5.07.

1. Y. Saito et al., Tetrahedron Letters, 1970, 4863.

B. L-(−)-γ-Amino-α-hydroxybutyric acid: To a solution of 1.5 g. (0.014 mole) of sodium carbonate in 40 ml. of water were added 5.3 g. (0.01 mole) of dehydroabietylammmonium-L-α-hydroxy-γ-phthalimidobutyrate and 60 ml. of ether. The mixture was shaken vigorously until all of the solid had dissolved. The ether layer was separated. The aqueous solution was washed twice with 20 ml. portions of ether and evaporated to 15 ml. under reduced pressure. To the concentrate was added 10 ml. of concentrated hydrochloric acid and the mixture was refluxed for ten hours. After cooling,

| TLC (silica gel F254; ninhydrin Solvent System | RF value 6'-Cbz-Kanamycin A | | Kanamycin A |
|---|---|---|---|
| n-PrOH—Pyridine-AcOH—$H_2O$ (15:10:3:12) | 0.42 (main) | 0.33  0.15 minor | 0.04 |
| Acetone-AcOH—$H_2O$ (20:6:74) | | 0.24 | 0.14 |
| $CHCl_3$—MeOH—c.$NH_4OH$—$H_2O$ (1:4:2:1) | | 0.76 | 0.50 |
| AcOMe—n-PrOH—C.$NH_4OH$ (45:105:60) | | 0.22* | 0.04* |

*Detected by anthrone-sulfuric acid.

The final product was found to be accompanied by two minor components by TLC with one of the solvent systems tested. However, the final product was used without further purification for the preparation of BB-K8 (I).

EXAMPLE 5

Preparation of L-(−)-γ-amino-α-hydroxybutyric acid from ambutyrosin A or B or mixtures thereof Ambutyrosin A (5.0 gm.) [U.S. Pat. No. 3,541,078, issued Nov. 17, 1970] was refluxed with 160 ml. of 0.5 N sodium hydroxide for one hour. The hydrolysate was neutralized with 6N HCl and chromatographed on a column of CG-50 ($NH_4^+$ type). The desired L-(−)-γ-amino-α-hydroxybutyric acid was isolated by developing the column with water and removing the water by freeze drying. The L-(−)-γ-amino-α-hydroxybutyric acid is characterized as a crystalline material having a m.p. of 212.5°–214.5° C. [Column 2, lines 31–38, U.S. Pat. No. 3,541,078].

EXAMPLE 6

Preparation of L-(−)-γ-amino-α-hydroxybutyric acid from DL-α-hydroxy-γ-phthalimidobutyric acid A. Dehydroabietylammonium L-α-hydroxy-γ-phthalimidobutyrate: To a solution of 25 g. (0.1 mole) of 2-hydroxy-γ-phthalimidobutyric acid[1] in 200 ml. of ethanol was added a solution of 29 g. (0.1 mole) of dehydroabietylamine in 130 ml. of ethanol. The solution was shaken vigorously for a minute and stood at separated phthalic acid was removed by filtration. The filtrate was evaporated under reduced pressure. The residue was dissolved in 10 ml. of water and the solution was evaporated to dryness. This operation was repeated twice to remove excess hydrochloric acid. The residual syrup was dissolved in 10 ml. of water and filtered to remove a small amount of insoluble phthalic acid. The filtrate was adsorbed on a column of IR-120 ($H^+$, 1 cm. × 35 cm.), the column was washed with 300 ml. of water and eluted with 1 N ammonium hydroxide solution. The eluate was collected in 15-ml. fractions. The ninhydrin positive fractions 10 to 16 were combined and evaporated under reduced pressure to give a syrup which crystallized gradually. The crystals were triturated with ethanol, filtered and dried in a vacuum desiccator to give 0.78 g. (66%) of L-(−)-γ-amino-α-hydroxybutyric acid. M.p. 206°–207° C. $[\alpha]_D^{24}$ −29° (C. 2.5, $H_2O$). The IR spectrum was identical with the authentic sample which was obtained from ambutyrosin.

EXAMPLE 7

Preparation of 6'-Carbobenzoxy-1,3,3''-tri-p-nitrobenzalkanamycin A (IIIa)

6'-Carbobenzoxykanamycin A (9.0 g., 14.5 m. moles) was suspended in 500 ml. of absolute ethanol at 24° C. and 8.7945 g. (58.2 millimoles) of p-nitrobenzaldehyde was added. The mixture was heated to reflux. During this time the mixture changed to a clear, yellow solution, but at reflux a white solid quickly began to form. The mixture was heated at reflux for 3 hours, then cooled, and the product collected by filtration and washed with a little absolute ethanol. The yield was 14.0 g. (94.5%) of white, crystalline solid, m.p. 233°–234° (uncorrected), of the title product IIIa.

Anal. calc'd. for $C_{47}H_{51}N_7O_{19}$: C, 55.46; H, 5.05; N, 9.63. Found: C, 55.39; H, 5.08; N, 9.60.

EXAMPLE 8

Preparation of 1-[L-(−)-γ-amino-α-hydroxybutyryl]-kanamycin A (IV) via IIIa.

6′-Carbobenzoxy-1,3,3,″-tri-p-nitrobenzalkanamycin A (5.0 g., 4.91 m. moles) was dissolved in 50 ml. of dimethylformamide (DMF) at 24° C. L-(−)-γ-benzyloxycarbonylamino-α-hydroxybutyric acid N-hydroxysuccinimide ester (2.064 g., 5.895 m.moles) was dissolved in 20 ml. of DMF at 24° C. and added slowly with vigorous stirring to the solution of the Schiff's base (III) over 75 minutes. The solution was stirred at 24° overnight. Using steam-ejector vacuum, the solution was flashed dry at about 40° C. It was then flashed repeatedly with methanol (100 ml.), to yield a viscous oil. The oil was dissolved in 100 ml. of 1:1 dioxane:$H_2O$ and 10 ml. of glacial acetic acid was added. The solution was placed in a 500 ml. Parr bottle, together with 2.5 g. of 5% Pd/C (Engelhard) and reduced at 45 psi $H_2$ for 4 hours at 24° C. The total pressure drop in this time (closed bottle) was 87 psi, including periodic repressurizations. The mixture was filtered through a pad of diatomaceous earth which was then washed with 3×50 ml. of 50% aqueous dioxane. The combined filtrates were flashed dry and azeotroped with n-butanol (100 ml.) and finally flashed repeatedly with methanol, giving a viscous oil. It was dissolved in 30 ml. of methanol and slowly poured into 1000 ml. of cold (5°–10° C.) diethyl ether with vigorous stirring. After stirring the resulting suspension for one-half hour in an ice bath, the precipitate was collected by filtration and immediately dried in a vacuum desiccator over $P_2O_5$. The product mixture weighed 4.9620 g. TLC (thin layer chromatography) showed it to consist mainly of compound IV, kanamycin A, and some traces of di and trisubstituted kanamycin A, and including 4-amino-2-hydroxybutyric acid.

The various fractions were separated using a 40 × 100 mm. glass column packed with Amberlite IRC-50 ($NH_4^+$ form, Type I, 100/200 mesh) to provide a resin bed of ca. 980 mm. The column was charged with 4.600 g. of the crude mixture dissolved in 15 ml. of water. The column was eluted with a gradient from $H_2O$ to 2 N $NH_4OH$, the elute being collected in 15 ml. fractions. 295 fractions were collected, then the column was washed with 1.5 l. of 3 N $NH_4OH$. Fractions were pooled on the basis of optical rotations, and solids isolated therefrom by lyophylizing.

In this run, the ratio of BB-K8/kana A was 0.45.

Compound IV, as recovered from this process, is identical with authentic product obtained by the method described in co-pending application, Ser. No. 221,378. M.p. 194° (dec.) $[\alpha]_D^{21}$ +85° (c=2, $H_2O$). Relative potency against B. subtilis (agar plate)=960 mcg./mg. (standard: kanamycin A free base).

Anal. calc'd. for $C_{22}H_{43}N_5O_{13}\cdot 2H_2CO_3$: C, 40.62; H, 6.68; N, 9.87. Found: C, 40.21; 39.79; H, 6.96, 6,87; N, 9.37, 9.49.

EXAMPLE 9

Preparation of the Monosulfate Salt of 1-[L-(−)-γ-amino-α-hydroxybutyryl]kanamycin A One mole of 1-[L-(−)-γ-amino-α-hydroxybutyryl]-kanamycin A is dissolved in 1 to 3 liters of water. The solution is filtered to remove any undissolved solids. To the chilled and stirred solution is added one mole of sulfuric acid dissolved in 500 ml. of water. The mixture is allowed to stir for 30 minutes, following which cold ethanol is added to the mixture till precipitation occurs. The solids are collected by filtration and are determined to be the desired monosulfate salt.

EXAMPLE 10

Preparation of the Disulfate Salt of 1-[L-(−)-γ-amino-α-hydroxybutyryl]kanamycin A (BB-K8·2$H_2SO_4$)

Thirty-five grams of 1-[L-(−)-γ-amino-α-hydroxybutyryl]kanamycin A (as the monobicarbonate trihydrate) was dissolved in 125 ml. of deionized water. A pH of approximately 9.0 was noted. The pH was lowered to 7–7.5 with 50% V/V sulfuric acid.

Eight and one half grams of Darco G-60 (activated charcoal) was added and the mixture was slurried at ambient room temperature for 0.5 hour. The carbon was removed by suitable filtration and washed with 40 ml. of water. The water wash was added to the filtrate.

The combined filtrate-wash above was adjusted to pH 2–2.6 with 50% V/V sulfuric acid. A large amount of carbon dioxide was evolved. The solution was left at house vacuum with stirring for 20 minutes to expel additional carbon dioxide.

Eight and one half grams of Darco G-60 was added to the degassed solution. The mixture was slurried for 0.5 hour at ambient room temperature. The carbon was removed by suitable filtration and washed with 35 ml. of deionized water. The water was added to the filtrate.

The combined filtrate-wash was adjusted to pH 1–1.3 with 50% V/V sulfuric acid. This solution was added with rapid stirring over a 10 minute period to 600–800 ml. of methanol (3–4 volumes of methanol). The mixture was stirred for 5 minutes at pH 1–1.3, passed through a 100 mesh screen, stirred for 2 minutes and allowed to settle for 5 minutes. Most of the supernatant was decanted. The remaining slurry was suitably filtered, washed with 200 ml. of methanol and vacuum dried at 50° C. for 24 hours. The yield of amorphous BB-K8·(dihydrogen sulfate)$_2$ was 32–34 grams; $[\alpha]_D^{22}$ $H_2O$=+74.75, decomposition at 220°–23° C.

| Fraction No. | Composition | Weight Grams | Correction to Weight of Whole Crude-Grams | Bioassay | % Yield |
|---|---|---|---|---|---|
| 120–150 | kana A | 1.1654 | 1.257 | 809 | 42.6 |
| 201–224 | BB-K29 | 0.40 | 0.43 | — | |
| 228–241 | BB-K8 | 0.6523 | 0.7036 | 786±101* | 19.2** |

*Average of 4 plate assays, ± standard deviation.
**If credit is taken for recovered kana A, the conversion to BB-K8 (IV) was 33.5%.

| Elemental Analysis (On Dry Basis*) | | |
|---|---|---|
| | Found | Theory |
| % C | 32.7, 33.5, 32.3 | 33.5 |
| % N | 8.78, 8.7, 8.2 8.8 | 8.97 |
| % S | 8.75, 8.9, 7.8, 8.85 | 8.2 |
| % Ash | nil | — |

*Karl Fisher water content: 2.33, 1.79, 2.87% (theory for monohydrate is 2.25% water). This salt is hygroscopic but not deliquescent. After storage of an aliquot in air at room temperature for 18 hours the water content increased to 9.55, 9.89% (theory for a pentahydrate is 10.33% water).

EXAMPLE 11

Preparation of 6'-Carbobenzoxy-1,3,3'-tri-salicylalkanamycin A (IIIb)

Substitution in the procedure of example 7 for the p-nitrobenzaldehyde used thereon of an equimolar quantity of salicylaldehyde produced the title compound IIIb; m.p. 192°–194° C. Upon drying, the m.p. was 196°–198° C.

Anal. calc'd. for $C_{47}H_{54}N_4O_{16}$: C, 60.62; H, 5.86; N, 6.02. Found: C, 58.67; H, 5.73; N, 5.98; Karl Fischer Water, 2.45.

Anal. corrected for water: Found: C, 60.14; H, 5.60; N, 6.13.

The nomenclature salicylalkanamycin A is equivalent to salicylidenekanamycin A according to Chemical Abstracts and shall be so for the purpose of this disclosure.

EXAMPLE 12

Preparation of 1-[L-(–)-γ-amino-α-hydroxybutyryl]kanamycin A (IV) via IIIb

Substitution in the procedure of example 8 for the 6'-carbobenzoxy-1,3,3'-tri-p-nitrobenzalkanamycin A used therein of an equimolar quantity of 6'-carbobenzoxy-1,3,3'-tri-p-salicylalkanamycin A (IIIb) produced compound IV.

We claim:

1. In the process for the preparation of the compound having the formula by more selectively acylating the 1-amino function of kanamycin A, the improvement which comprises converting the 1,3 and 3''-amino groups of 6'-carbobenzoxykanamycin A, compound II, into Schiff base moieties prior to acylation with L-(–)-γ-benzyloxycarbonyl-amino-γ-hydroxybutyric acid N-hydroxysuccinimide ester by treating 1 mole of 6'-carbobenzoxykanamycin A (II) with at least three moles of an aldehyde selected from the group comprising 4-nitrobenzaldehyde, benzaldehyde, salicylaldehyde, 4-methoxybenzaldehyde and pivaldehyde, in a (lower)alkanol, at elevated temperatures, for at least 2 hours, to produce the compound having the formula

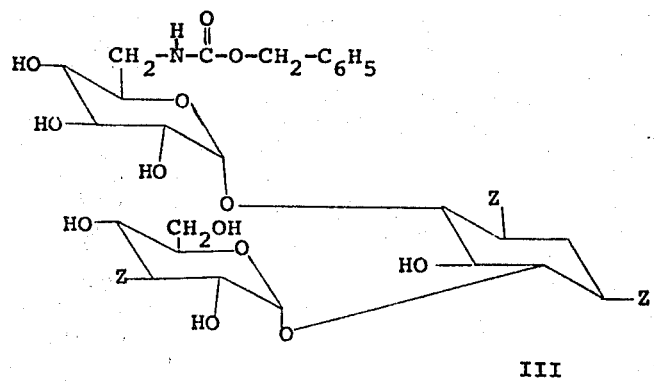

III in which Z is

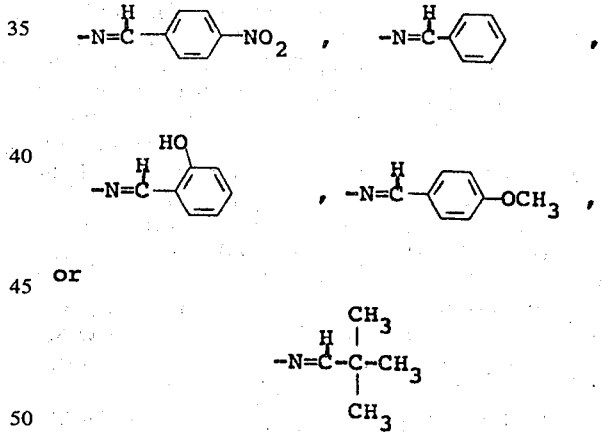

or

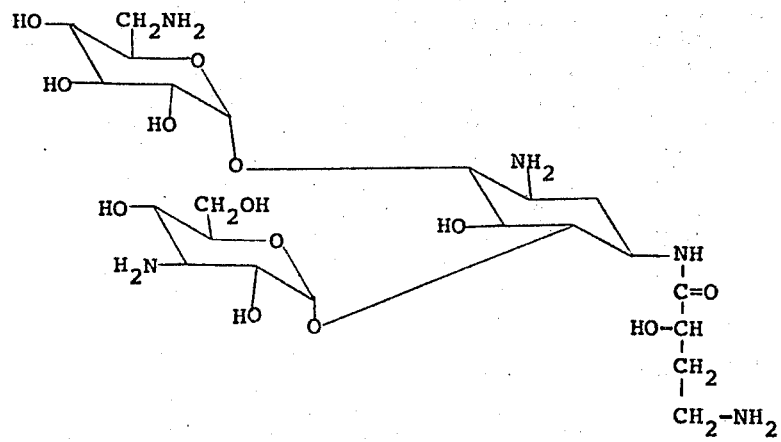

IV and hydrogenating the resultant intermediate to produce the compound of Formula IV.

2. In the process of claim 1, treating one mole of compound II with 3 to 6 moles of aldehyde, in a (lower-)alkanol selected from the group comprising absolute ethanol, methanol, n-propanol, isopropanol, n-butanol, sec-butanol, tert-butanol, or mixtures thereof, at temperatures in the range of 50° C. to about reflux temperature of the system, for a period of 2 to 10 hours, to produce compound III.

3. In the process of claim 1, treating one mole of compound II with 3.5 to 4.5 moles of p-nitrobenzaldehyde salicylaldehyde or benzaldehyde in absolute ethanol, methanol, m-propanol or isopropanol at about reflux temperature for a period of about 2 to 4 hours to produce compound III in which Z is

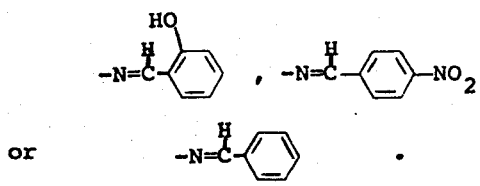

4. In the process of claim 1, treating one mole of compound II with about four moles of p-nitrobenzaldehyde in absolute ethanol at about reflux for a period of about 2 to 4 hours to produce compound III in which Z is

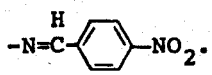

5. In the process of claim 1, treating one mole of compound II with about four moles of salicylaldehyde in absolute ethanol at about reflux temperature for a period of about 2 to 4 hours to produce compound III in which Z is

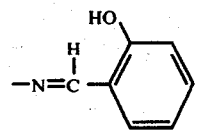

* * * * *

UNITED STATES PATENT OFFICE
CERTIFICATE OF CORRECTION

Patent No. 3,974,137   Dated August 10, 1976

Inventor(s)  Richard H. Schreiber and John G. Keil

It is certified that error appears in the above-identified patent and that said Letters Patent are hereby corrected as shown below:

Column 20, lines 5 and 6, "L-(-)-γ-benzyloxycarbonylamino-γ-hydroxybutyric" should read --L-(-)-γ-benzyloxycarbonylamino-α-hydroxybutyric--.

In Claim 3, line 4, "m-propanol" should read --n-propanol--.

Signed and Sealed this

Second Day of November 1976

[SEAL]

Attest:

RUTH C. MASON
Attesting Officer

C. MARSHALL DANN
Commissioner of Patents and Trademarks